United States Patent
Mleziva et al.

[19]

[11] Patent Number: 6,057,024

[45] Date of Patent: May 2, 2000

[54] COMPOSITE ELASTIC MATERIAL WITH RIBBON-SHAPED FILAMENTS

[75] Inventors: Mark Michael Mleziva, Appleton, Wis.; Richard Macferran Shane, Lilburn, Ga.; Donald Vincent Willitts, Powder Springs, Ga.; Oomman Painumoottil Thomas, Alpharetta, Ga.; James Russell Fitts, Jr., Gainesville, Ga.; Marion Clyde Morris, Appleton, Wis.

[73] Assignee: Kimberly-Clark Worldwide, Inc., Neenah, Wis.

[21] Appl. No.: 08/961,523

[22] Filed: Oct. 31, 1997

[51] Int. Cl.[7] ........................................................ B23B 3/28
[52] U.S. Cl. .......................... 428/114; 428/181; 428/198; 442/329; 156/161; 156/164; 156/166; 156/178; 156/179; 156/290
[58] Field of Search ...................................... 428/109, 110, 428/114, 179, 181, 198, 182; 442/329, 337; 156/161, 164, 166, 178, 179, 290

[56] References Cited

U.S. PATENT DOCUMENTS

| | | |
|---|---|---|
| 3,463,652 | 8/1969 | Whitesel et al. . |
| 3,468,748 | 9/1969 | Bassett . |
| 3,485,706 | 12/1969 | Evans . |
| 3,549,470 | 12/1970 | Greenwald et al. . |
| 3,575,752 | 4/1971 | Carpenter . |
| 3,575,782 | 4/1971 | Hansen . |
| 3,576,931 | 4/1971 | Chopra et al. . |
| 3,692,618 | 9/1972 | Dorschner et al. . |
| 3,749,241 | 7/1973 | Matsuzaki et al. . |
| 3,802,817 | 4/1974 | Matsuki et al. . |
| 3,849,241 | 11/1974 | Butin et al. . |
| 3,884,030 | 5/1975 | Baxter et al. . |
| 3,969,471 | 7/1976 | Driscoll . |
| 3,969,472 | 7/1976 | Driscoll . |
| 4,028,452 | 6/1977 | Driscoll . |
| 4,062,915 | 12/1977 | Stricharczuk et al. . |
| 4,085,175 | 4/1978 | Keuchel . |
| 4,100,324 | 7/1978 | Anderson et al. . |
| 4,176,978 | 12/1979 | Ruzicka et al. . |
| 4,180,536 | 12/1979 | Howell, Jr. et al. . |
| 4,188,448 | 2/1980 | Stricharczuk et al. . |
| 4,209,563 | 6/1980 | Sisson . |
| 4,259,220 | 3/1981 | Bunnelle et al. . |
| 4,264,670 | 4/1981 | Kontos . |
| 4,279,848 | 7/1981 | Baxter et al. . |
| 4,282,890 | 8/1981 | Howell, Jr. et al. . |
| 4,340,563 | 7/1982 | Appel et al. . |
| 4,418,123 | 11/1983 | Bunnelle et al. . |
| 4,483,897 | 11/1984 | Fujimura et al. . |
| 4,485,141 | 11/1984 | Fujimura et al. . |
| 4,543,099 | 9/1985 | Bunnelle et al. . |
| 4,552,795 | 11/1985 | Hansen et al. . |
| 4,562,022 | 12/1985 | Li et al. . |
| 4,626,390 | 12/1986 | Li et al. . |
| 4,640,859 | 2/1987 | Hansen et al. . |
| 4,663,220 | 5/1987 | Wisneski et al. . |
| 4,680,213 | 7/1987 | Fourezon . |
| 4,687,477 | 8/1987 | Suzuki et al. . |
| 4,719,261 | 1/1988 | Brunnelle et al. . |
| 4,720,415 | 1/1988 | Vander Wielen et al. . |
| 4,728,472 | 3/1988 | Windley . |
| 4,734,311 | 3/1988 | Sokolowski . |
| 4,741,949 | 5/1988 | Morman et al. . |
| 4,753,762 | 6/1988 | Li et al. . |
| 4,753,834 | 6/1988 | Braun et al. . |
| 4,781,966 | 11/1988 | Taylor . |

(List continued on next page.)

FOREIGN PATENT DOCUMENTS

| | | |
|---|---|---|
| 995430 | 8/1976 | Canada . |
| 1023118 | 12/1977 | Canada . |
| 1042167 | 11/1978 | Canada . |
| 1068889 | 1/1980 | Canada . |
| 1107025 | 8/1981 | Canada . |
| 1147113 | 5/1983 | Canada . |
| 1152879 | 8/1983 | Canada . |
| 1154188 | 9/1983 | Canada . |
| 1164135 | 3/1984 | Canada . |
| 1174548 | 9/1984 | Canada . |
| 1199462 | 1/1986 | Canada . |
| 1246979 | 12/1988 | Canada . |
| 2015158 | 10/1990 | Canada . |
| 1280062 | 2/1991 | Canada . |
| 1281271 | 3/1991 | Canada . |
| 2028510 | 4/1991 | Canada . |
| 1293433 | 12/1991 | Canada . |
| 1295103 | 2/1992 | Canada . |
| 2053520 | 5/1992 | Canada . |
| 0338854 | 10/1989 | European Pat. Off. . |
| 0586924 | 3/1994 | European Pat. Off. . |
| 2148588 | 3/1973 | Germany . |
| 68027551 | 7/1967 | Japan . |
| 70018727 | 9/1967 | Japan . |
| 48-063025 | 5/1973 | Japan . |
| 49-014730 | 2/1974 | Japan . |
| 49-061414 | 6/1974 | Japan . |
| 50-077616 | 6/1975 | Japan . |
| 6903634 | 9/1970 | Netherlands . |
| 1318964 | 5/1973 | United Kingdom . |
| 96 41041 | 12/1996 | WIPO ............................. D01D 5/30 |

OTHER PUBLICATIONS

John A. Manson and Leslie H. Sperling, *Polymer Blends And Composites*, Plenum Press, A Division of Plenum Publishing Corp., New York, 1976, pp. 273–277.

Kirk–Othmer, *Encyclopedia of Chemical Tecnology, Fourth Edition*, John Wiley & Sons, Inc., New York, 1996, pp. 765–767.

*Primary Examiner*—Christopher Raimund
*Attorney, Agent, or Firm*—Pauley Petersen Kinne & Fejer

[57] ABSTRACT

A composite elastic material includes a layer of ribbon-shaped elastomeric elements disposed in machine direction alignment and point bonded to an extensible layer which may be a gatherable layer or a stretchable layer. A layer of meltblown elastomeric fibers may be bonded to the layer of elastomeric ribbon-shaped elements before bonding to the extensible layer. The elastic composite has excellent cohesion, controlled breathability to air and water vapor, an opaque appearance, and is easy to cut and convert to end use products such as garments, pads, diapers, and personal care products where elasticity is desired.

40 Claims, 6 Drawing Sheets

U.S. PATENT DOCUMENTS

| | | |
|---|---|---|
| 4,787,699 | 11/1988 | Moulin . |
| 4,803,117 | 2/1989 | Daponte . |
| 4,842,666 | 6/1989 | Werenicz . |
| 4,858,629 | 8/1989 | Cundari . |
| 4,892,903 | 1/1990 | Himes . |
| 4,910,064 | 3/1990 | Sabee . |
| 4,977,011 | 12/1990 | Smith . |
| 5,093,422 | 3/1992 | Himes . |
| 5,108,820 | 4/1992 | Kaneko et al. . |
| 5,108,827 | 4/1992 | Gessner . |
| 5,124,098 | 6/1992 | Vischer . |
| 5,200,246 | 4/1993 | Sabee . |
| 5,209,801 | 5/1993 | Smith . |
| 5,219,633 | 6/1993 | Sabee . |
| 5,232,777 | 8/1993 | Sipinen et al. . |
| 5,304,162 | 4/1994 | Kuen ........................................ 604/391 |
| 5,304,599 | 4/1994 | Himes . |
| 5,332,613 | 7/1994 | Taylor et al. . |
| 5,334,437 | 8/1994 | Zafiroglu . |
| 5,336,552 | 8/1994 | Strack et al. . |
| 5,342,469 | 8/1994 | Bodford et al. .................... 156/244.22 |
| 5,366,793 | 11/1994 | Fitts, Jr. et al. . |
| 5,368,925 | 11/1994 | Hosokawa et al. . |
| 5,382,400 | 1/1995 | Pike et al. . |
| 5,385,775 | 1/1995 | Wright . |
| 5,413,849 | 5/1995 | Austin et al. . |
| 5,431,644 | 7/1995 | Sipinen et al. . |
| 5,431,991 | 7/1995 | Quantrille et al. . |
| 5,472,775 | 12/1995 | Obijeski et al. . |
| 5,498,468 | 3/1996 | Blaney . |
| 5,523,146 | 6/1996 | Bodford et al. ........................ 428/198 |
| 5,540,976 | 7/1996 | Shawver et al. . |
| 5,755,902 | 5/1998 | Reynolds ............................... 156/73.1 |

COMPOSITE ELASTIC MATERIAL WITH RIBBON-SHAPED FILAMENTS

FIELD OF THE INVENTION

The present invention relates to an improved composite elastic material including a layer of elastic ribbon-shaped filaments, and a method of making the laminates.

BACKGROUND OF THE INVENTION

Composites of elastic and nonelastic materials have been made by bonding nonelastic materials to elastic materials in a manner that allows the entire composite to stretch or elongate so they can be used in garment materials, pads, diapers and personal care products where elasticity may be desired.

One such composite material is disclosed in U.S. Pat. No. 5,385,775, issued to Wright. That patent discloses a composite elastic material adapted to provide improved tenacity in one direction. The material includes: (1) an anisotropic elastic fibrous web having at least one layer of elastomeric meltblown fibers and at least one layer of elastomeric filaments autogenously bonded to at least a portion of the elastomeric meltblown fibers, and (2) at least one gatherable layer joined at spaced-apart locations to the anisotropic elastic fibrous web so that the gatherable layer is gathered between the spaced-apart locations. The gatherable layer is joined to the elastic fibrous web when the elastic web is in a stretched condition so that when the elastic web relaxes, the gatherable layer gathers between the spaced-apart bonding locations.

In another composite material, a nonelastic material is joined to an elastic sheet while the elastic sheet is in a stretched condition so that when the elastic sheet relaxes, the nonelastic material gathers between the locations where it is bonded to the elastic sheet. The resulting composite elastic material is stretchable to the extent that the nonelastic material gathered between the bond locations allows the elastic sheet to elongate. An example of this type of composite material is disclosed, for example, by U.S. Pat. No. 4,720,415 to Vander Wielen et al., issued Jan. 19, 1988.

U.S. Pat. No. 3,468,748 discloses a nonwoven fabric having machine direction elasticity which contains at least one fibrous web and a plurality of elastic cords, strings, bands, etc., which are joined to the fibrous web while the elastic material is stretched. Upon release of the stretching force, the elastic material contracts from its extended condition and puckers the fibrous material. U.S. Pat. No. 3,575,782 discloses an elastic material which contains partially extended spaced elastic yarns sealed between two gathered fibrous webs. Elastic yarns are stretched, joined to the fibrous webs with a binder and then passed through a drying oven. Tension on the elastic yarn relaxed and more heat is applied to cause the elastic yarns to retract or shrink, creating a shirred elastic material.

Other patents disclose reinforced textile matrices and stabilized continuous filament webs in which threads or molecularly oriented continuous filaments are stabilized in a substantially parallel relationship. For example, U.S. Pat. No. 4,680,213 discloses a reinforced textile matrix and U.S. Pat. No. 4,910,064 discloses a substantially parallel array of molecularly oriented continuous filaments stabilized by meltblown fibers to create a coherent nonwoven fibrous web.

U.S. Pat. No. 4,734,311, issued to Sokolowski, discloses an elasticized nonwoven fiber material made by combining textile fibers with elasticizable fibers and bonding them together. The bonded web is heat treated to heat shrink the web. U.S. Pat. No. 3,468,748, issued to Bassett, discloses a nonwoven fabric including a bonded web of individualized fibers, and elastomeric strands secured to the web to provide buckled regions in the web. U.S. Pat. No. 5,540,976, issued to Shawver et al., discloses a nonwoven fabric laminate having cross-directional stretch properties. The laminate includes an inner elastic polymer layer sandwiched between two outer crimpable spunbond nonwoven webs.

SUMMARY OF THE INVENTION

The present invention is a composite elastic material including at least one anisotropic elastic nonwoven web comprised of elastomeric ribbon-shaped elements, and at least one extensible layer joined to the anisotropic elastic nonwoven web. The extensible layer may include a gatherable layer joined at spaced-apart locations to the elastic web when the elastic web is in an elongated (stretched) state. When the elastic web is relaxed, the gatherable layer is gathered between the spaced-apart bonding locations. Alternatively, the extensible layer may be an elastomeric and/or other stretchable layer which is joined either continuously or at spaced apart locations to the elastic web.

The extensible layer may be a gatherable nonwoven web of fibers such as, for example, a web of spunbonded fibers, a web of meltblown fibers, a bonded carded web of fibers, or a multilayer material including at least one of the aforementioned webs. The extensible layer may also be a gatherable mixture of fibers and one or more other materials such as, for example, wood pulp, staple length fibers, particulates and superabsorbent materials. The extensible layer may also be a stretchable material including, for example, a knitted or woven fabric having a looped structure, an open woven gauze, a highly creped paper, an extensible nonwoven fabric, a knitted fabric, and/or a compressively pre-shrunk fabric web.

The anisotropic elastic fibrous web includes at least one layer of ribbon-shaped elastomeric elements. The ribbon-shaped elastomeric elements can be aligned in a machine direction, can be substantially parallel to one another, and/or can be in rows. The ribbon-shaped elastomeric elements may have a width and a thickness such that the width is at least two times as great as the thickness.

The use of ribbon-shaped elastic elements provides several process and product advantages compared to conventional filaments having round cross-sections. These advantages include increased cohesion between the elastomeric elements and the extensible layer(s) during and after processing, easier cutting or tearing of the elastic web due to a thinner cross-section, improved quenching due to increased surface area to volume ratios, and more uniform lay-down. Also, the ribbon-shaped elements make it easier to regulate breathability, opacity and porosity of the product by increasing or decreasing the element density (i.e. the number of elements per unit of cross-sectional area). Also, the breathability, opacity and porosity of the product can be regulated by proper design of the element geometry and density. Also, the laminate may exhibit improved stress relaxation due to the more film-like cross-section of the elastic web.

DEFINITIONS

As used herein, the term "ribbon-shaped elements" means thermoplastic polymer filaments, film strips, or other elongated elements having cross-sectional dimensions defining a flatness ratio of at least two. The "flatness ratio" is defined as the ratio of the longest cross-sectional dimension to the shortest cross-sectional dimension. For example, ribbon-shaped elements may have rectangular, elliptical, or dumbbell-shaped cross-sections.

The term "elastic" is used herein to mean any material which, upon application of a biasing force, is stretchable, that is, elongatable at least about 60 percent (i.e., to a stretched, biased length which is at least about 160 percent of its relaxed unbiased length), and which, without application of an external retraction force, will recover at least 55 percent of its elongation upon release of the stretching, elongating force. A hypothetical example would be a one (1) inch sample of a material which is elongatable to at least 1.60 inches and which, upon being elongated to 1.60 inches and released, will recover to a length of not more than 1.27 inches. Many elastic materials may be elongated by much more than 60 percent (i.e., much more than 160 percent of their relaxed length), for example, elongated 100 percent or more, and many of these will recover to substantially their initial relaxed length, for example, to within 105 percent of their original relaxed length, upon release of the stretching force.

The term "stretchable" is used herein to mean any material which, upon application of a biasing force, is elongatable at least about 50 percent and which, either with or without application of an external retraction force, will recover at least about 55% of its elongation upon release of the biasing force. Stretchable materials include both elastic materials and certain stretchable inelastic materials that will recover at least 55% when laminated to an elastic material or otherwise exposed to a retractive force.

The term "nonelastic" as used herein refers to any material which does not fall within the definition of "elastic," above.

The terms "recover" and "recovery" as used herein refer to a contraction of a stretched material upon termination of a biasing force following stretching of the material by application of the biasing force. For example, if a material having a relaxed, unbiased length of one (1) inch is elongated 50 percent by stretching to a length of one and one half (1.5) inches the material would be elongated 50 percent (0.5 inch) and would have a stretched length that is 150 percent of its relaxed length. If this exemplary stretched material contracted, that is recovered to a length of one and one tenth (1.1) inches after release of the biasing and stretching force, the material would have recovered 80 percent (0.4 inch) of its one-half (0.5) inch elongation. Recovery may be expressed as [(maximum stretch length minus final sample length)/(maximum stretch length minus initial sample length)]×100.

The term "machine direction" as used herein refers to the direction of travel of the forming surface onto which fibers are deposited during formation of a nonwoven fibrous web.

The term "cross-machine direction" as used herein refers to the direction which is perpendicular to the machine direction defined above.

The term "strength index" as used herein means a ratio of the tensile load of a material in the machine direction (MD) at a given elongation with the tensile load of that same material in the cross-machine direction (CD) at the same elongation. Typically, the tensile load is determined at an elongation which is less than the ultimate elongation of the material (i.e., elongation at break). For example, if the ultimate elongation of an elastic material is about 600 percent in both the machine and cross-machine directions, the tensile load may be measured at an elongation of about 400 percent. In that case, the strength index may be expressed by the following equation:

strength index=(MD tensile load at 400% elongation/CD tensile load at 400% elongation)

A material having a machine direction (MD) tensile load greater than its cross-machine direction (CD) tensile load will have a strength index that is greater than one (1). A material having a machine direction tensile load less than its cross-machine direction tensile load will have a strength index that is less than one (1).

The term "isotropic" as used herein refers to a material characterized by a strength index ranging from about 0.5 to about two (2), indicating similar properties in all directions.

The term "anisotropic" as used herein refers to material characterized by a strength index which is less than about 0.5 or greater than about two (2), indicating different properties in different directions. For example, an anisotropic nonwoven web may have a strength index of about 0.25 or about three (3).

The term "composite elastic material" as used herein refers to a multilayer material having at least one elastic layer joined to at least one extensible layer such that the extensible layer gathers or retracts when the elastic layer is relaxed. The extensible layer may be a gatherable layer (i.e. a layer which gathers between bond points) or a stretchable layer. A composite elastic material may be stretched to the extent that the extensible layer allows the elastic material to elongate. One type of composite elastic material is disclosed, for example, by U.S. Pat. No. 4,720,415 to Vander Wielen et al., issued Jan. 19, 1988, which is hereby incorporated by reference.

The term "tenacity" as used herein refers to the resistance to elongation of a composite elastic material which is provided by its elastic component. Tenacity is the tensile load of a composite elastic material at specified strain (i.e., elongation) for a given width material divided by the basis weight of that composite material's elastic component as measured at about the composite material's stretch-to-stop elongation. For example, the tenacity of a composite elastic material is typically determined in one direction (e.g., machine direction) at about the composite material's stretch-to-stop elongation. Elastic materials having high values for tenacity are desirable in certain applications because less material is needed to provide a specified resistance to elongation than a low tenacity material. For a specified sample width, tenacity is reported in units of force divided by the units of basis weight of the elastic component. This provides a measure of force per unit mass and is accomplished by reporting the basis weight of the elastic component and the grams of force required to stretch a particular width of the material to its stop length. For example, reported units may be $grams_{force}$ (for a specific sample width)/grams per square meter. Unless specified otherwise, all tenacity data is reported for the first extension of a three (3) inch wide sample having a four (4) inch gauge length.

As used herein the term "nonwoven web" means a web having a structure of individual fibers or threads which are interlaid, but not in an identifiable, repeating manner. Nonwoven webs have been, in the past, formed by a variety of processes such as, for example, melt-blowing processes, spunbonding processes and bonded carded web processes.

As used herein, the term "autogenous bonding" means bonding provided by fusion and/or self-adhesion of fibers and/or filaments without an applied external adhesive or bonding agent. Autogenous bonding may be provided by contact between fibers and/or filaments while at least a portion of the fibers and/or filaments are semi-molten or tacky. Autogenous bonding may also be provided by blending a tackifying resin with the thermoplastic polymers used to form the fibers and/or filaments. Fibers and/or filaments formed from such a blend can be adapted to self-bond with or without the application of pressure and/or heat. Solvents may also be used to cause fusion of fibers and filaments which remains after the solvent is removed.

As used herein, the term "meltblown fibers" means fibers formed by extruding a molten thermoplastic material through a plurality of fine, usually circular, die capillaries as molten threads or filaments into a high velocity gas (e.g. air) stream which attenuates the filaments of molten thermoplastic material to reduce their diameter, possibly to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin, the disclosure of which is hereby incorporated by reference.

As used herein, the term "spunbonded fibers" refers to small diameter fibers which are formed by extruding a molten thermoplastic material as filaments from a plurality of fine, usually circular, capillaries of a spinnerette with the diameter of the extruded filaments then being rapidly reduced as by, for example, eductive drawing or other well-known spunbonding mechanisms. The production of spunbonded nonwoven webs is illustrated in patents such as, for example, in U.S. Pat. No. 3,802,817 to Matsuki et al. and U.S. Pat. No. 5,382,400 to Pike et al. The disclosures of these patents are hereby incorporated by reference.

As used herein, the term "polymer" generally includes, but is not limited to, homopolymers, copolymers, such as, for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to, isotactic, syndiotactic and random symmetries.

As used herein the term "bicomponent fibers" refers to fibers which have been formed from at least two polymers extruded from separate extruders but spun together to form one fiber. The polymers are arranged in substantially constantly positioned distinct zones across the cross-section of the bicomponent fibers and extend continuously along the length of the bicomponent fibers. The configuration of such a bicomponent fiber may be, for example, a sheath/core arrangement wherein one polymer is surrounded by another or may be a side-by-side arrangement or an "islands-in-the-sea" arrangement. Bicomponent fibers are taught in U.S. Pat. No. 5,108,820 to Kaneko et al., U.S. Pat. No. 5,336,552 to Strack et al., and European Patent 0586924. For two component fibers, the polymers may be present in ratios of 75/25, 50/50, 25/75 or any other desired ratios.

As used herein the term "biconstituent fibers" refers to fibers which have been formed from at least two polymers extruded from the same extruder as a blend. The term "blend" is defined below. Biconstituent fibers do not have the various polymer components arranged in relatively constantly positioned distinct zones across the cross-sectional area of the fiber and the various polymers are usually not continuous along the entire length of the fiber, instead usually forming fibrils which start and end at random. Biconstituent fibers are sometimes also referred to as multiconstituent fibers. Fibers of this general type are discussed in, for example, U.S. Pat. No. 5,108,827 to Gessner. Bicomponent and biconstituent fibers are also discussed in the textbook *Polymer Blends and Composites* by John A. Manson and Leslie H. Sperling, copyright 1976 by Plenum Press, a division of Plenum Publishing Corporation of New York, IBSN 0-306-30831-2, at Pages 273 through 277.

As used herein the term "blend" means a mixture of two or more polymers while the term "alloy" means a sub-class of blends wherein the components are immiscible but have been compatibilized. "Miscibility" and "immiscibility" are defined as blends having negative and positive values, respectively, for the free energy of mixing. Further, "compatibilization" is defined as the process of modifying the interfacial properties of an immiscible polymer blend in order to make an alloy.

As used herein, the term "machine direction aligned" refers to ribbon-shaped elastic elements that extend more in the machine direction than in the cross-direction. The angle between the machine direction and the direction of orientation of such elements is less than about 45 degrees, and may be less than about 30 degrees, or even less than about 15 degrees.

As used herein, the term "superabsorbent" refers to absorbent materials capable of absorbing at least 10 grams of aqueous liquid (e.g. distilled water) per gram of absorbent material while immersed in the liquid for 4 hours and holding substantially all of the absorbed liquid while under a compression force of up to about 1.5 psi.

As used herein, the term "consisting essentially of" does not exclude the presence of additional materials which do not significantly affect the desired characteristics of a given composition or product. Exemplary materials of this sort would include, without limitation, pigments, antioxidants, stabilizers, surfactants, waxes, flow promoters, particulates and materials added to enhance processability of the composition.

DETAILED DESCRIPTION OF THE PRESENTLY PREFERRED EMBODIMENTS

The present invention provides a composite elastic material such as, for example, a stretch-bonded laminate which is adapted to provide increased opacity, controlled breathability and porosity, improved cutting, tearing and formation. This composite elastic material includes an anisotropic elastic fibrous web composed of ribbon-shaped elastomeric elements and alternatively, a thin coating of elastomeric meltblown fibers. Referring now to the drawings wherein like reference numerals represent the same or equivalent structure and, in particular, to FIG. 1 of the drawings there is schematically illustrated at 10 a process for forming a stretch-bonded laminate which includes an anisotropic elastic fibrous web 12 including ribbon-shaped elastomeric elements.

Figure 1:
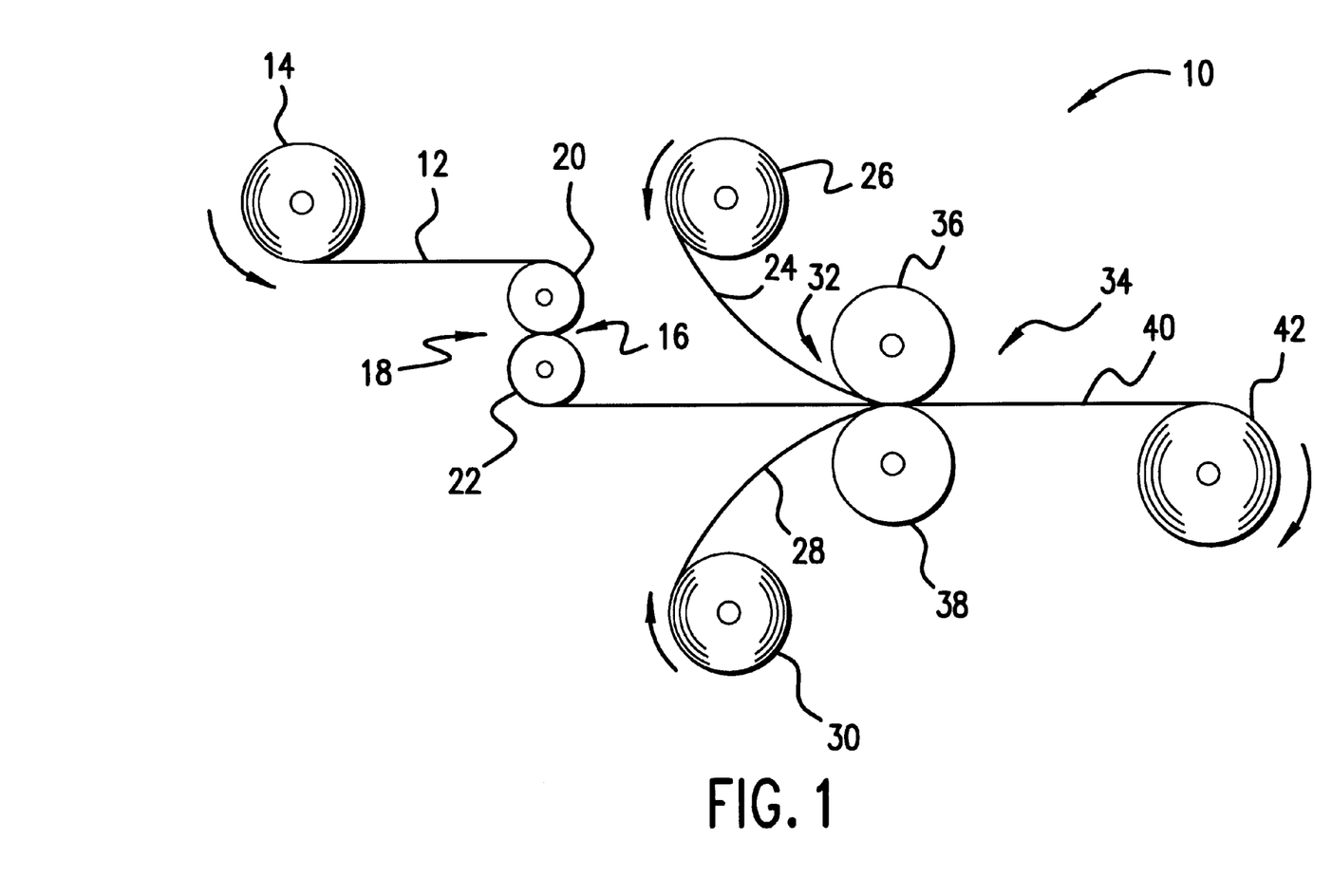
FIG. 1 is a schematic drawing of an exemplary process for forming a composite elastic material of the invention.

According to the present invention, an anisotropic elastic fibrous web 12 is unwound from a supply roll 14 and travels in the direction indicated by the arrow associated therewith as the supply roll 14 rotates in the direction of the arrows associated therewith. The anisotropic elastic fibrous web 12 passes through a nip 16 of the S-roll arrangement 18 formed by the stack rollers 20 and 22.

The anisotropic elastic fibrous web 12 may also be formed in a continuous process such as, for example, the process described below, and passed directly through the nip 16 without first being stored on a supply roll.

A first extensible layer 24 is unwound from a supply roll 26 and travels in the direction indicated by the arrow associated therewith as the supply roll 26 rotates in the direction of the arrows associated therewith. A second extensible layer 28 is unwound from a second supply roll 30 and travels in the direction indicated by the arrow associated therewith as the supply roll 30 rotates in the direction of the arrows associated therewith.

The first extensible layer 24 and second extensible layer 28 pass through the nip 32 of the bonder roller arrangement 34 formed by the bonder rollers 36 and 38. The first extensible layer 24 and/or the second extensible layer 28 may be formed by extrusion processes such as, for example, meltblowing processes, spunbonding processes or film extrusion processes and passed directly through the nip 32 without first being stored on a supply roll.

The anisotropic elastic fibrous web 12 passes through the nip 16 of the S-roll arrangement 18 in a reverse-S path as indicated by the rotation direction arrows associated with the stack rollers 20 and 22. From the S-roll arrangement 18, the anisotropic elastic fibrous web 12 passes through the pressure nip 32 formed by a bonder roller arrangement 34. Additional S-roll arrangements (not shown) may be introduced between the S-roll arrangement and the bonder roller arrangement to stabilize the stretched material and to control the amount of stretching. Because the peripheral linear speed of the rollers of the S-roll arrangement 18 is controlled to be less than the peripheral linear speed of the rollers of the bonder roller arrangement 34, the anisotropic elastic fibrous web 12 is tensioned between the S-roll arrangement 18 and the pressure nip of the bonder roll arrangement 32. Importantly, the ribbon-shaped filaments of the anisotropic elastic fibrous web 12 should run along the direction that web is stretched so that they can provide the desired stretch properties in the finished composite material. By adjusting the difference in the speeds of the rollers, the anisotropic elastic fibrous web 12 can be tensioned so that it stretches a desired amount and is maintained in such stretched condition while the first extensible layer 24 and second extensible layer 28 are joined to the anisotropic elastic fibrous web 12 during their passage through the bonder roller arrangement 34 to form a composite elastic material 40. For instance, the elastic fibrous web may be stretched to about 1.1–10 times its original length, desirably about 2–7 times its original length, commonly about 3–5 times its original length. If the extensible layers 24 and 28 are gatherable materials as described below, the prestretching of the elastic fibrous web 12 before bonding is especially important. If the extensible layers 24 and 28 are stretchable materials, the prestretching of the elastic fibrous web 12 is not essential.

The composite elastic material 40 immediately relaxes upon release of the tensioning force provided by the S-roll arrangement 18 and the bonder roll arrangement 34, whereby the first extensible layer 24 and the second extensible layer 28 may gather in the composite elastic material 40. The composite elastic material 40 is then wound up on a winder 42. Processes of making composite elastic materials of this type are described in, for example, U.S. Pat. No. 4,720,415, the disclosure of which is hereby incorporated by reference.

The extensible layers 24 and 28 may be gatherable nonwoven materials such as, for example, spunbonded polymeric webs, meltblown polymeric webs, bonded carded webs, and/or thermoplastic films. The fibrous web 12 may be composed of a single polymer or may include biconstituent or bicomponent fibers as defined above. In one embodiment of the present invention, one or both of the extensible layers 24 and 28 is a multilayer material having, for example, at least one layer of spunbonded web joined to at least one layer of meltblown web, bonded carded web or other suitable material.

A wide variety of thermoplastic polymer materials can be used to make the extensible layers 24 and 28. Exemplary polymer materials include without limitation polypropylene, polyethylene (high and low density), ethylene copolymers with $C_3$–$C_{20}$ α-olefins, propylene copolymers with ethylene or $C_4$–$C_{20}$ α-olefins, butene copolymers with ethylene, propylene or $C_5$–$C_{20}$ α-olefins, polyvinyl chloride, polyesters, polyamides, polyfluorocarbons, polyurethane, polystyrene, polyvinyl alcohol, caprolactams, and cellulosic and acrylic resins.

One or both of the extensible layers 24 and 28 may also be a gatherable composite material made of a mixture of two or more different fibers or a mixture of fibers and particulates. Such mixtures may be formed by adding fibers and/or particulates to the gas stream in which meltblown fibers are carried so that an intimate entangled commingling of meltblown fibers and other materials, e.g., wood pulp, staple fibers and particulates such as, for example, hydrocolloid (hydrogel) particulates commonly referred to as superabsorbent materials, occurs prior to collection of the meltblown fibers upon a collecting device to form a coherent web of randomly dispersed meltblown fibers and other materials such as disclosed in U.S. Pat. No. 4,100,324, the disclosure of which is hereby incorporated by reference.

One or both of the extensible layers 24 and 28 may be gatherable layers made of pulp fibers, including wood pulp fibers, to form a material such as, for example, a tissue layer. Additionally, the layers 24 and 28 may be layers of hydraulically entangled fibers such as, for example, hydraulically entangled mixtures of wood pulp and staple fibers such as disclosed in U.S. Pat. No. 4,781,966, the disclosure of which is hereby incorporated by reference.

The extensible layers 24 and 28 may alternatively include stretchable layers or materials that do not require gatherability in order for the composite laminate to have elastic properties. As explained above, a stretchable layer may be an elastic layer or, alternatively, an inelastic layer that is stretchable by at least 50% of its original length and may be recovered upon application of an external retractive force, such as by the retraction of an elastic layer laminated to the stretchable layer. Examples of stretchable layers include without limitation elastic and inelastic materials including knitted or woven fabrics having looped structures, open woven gauze designed for high extensibility, highly creped papers, extensible nonwoven fabrics (including those made primarily from entangled polyester as described in U.S. Pat. No. 3,485,706), compressively pre-shrunk fabrics, other knitted fabrics, and extensible thermoplastic films.

The extensible layers 24 and 28 may be joined to the anisotropic elastic fibrous web 12 in at least at two places by any suitable means such as, for example, thermal bonding or ultrasonic welding which softens at least portions of at least one of the materials, usually the elastic fibrous web because the elastomeric materials used for forming the anisotropic elastic fibrous web 12 have lower softening points than the components of the gatherable layers 24 and 28. Joining may be produced by applying heat and/or pressure to the overlaid anisotropic elastic fibrous web 12 and the gatherable layers 24 and 28 by heating these portions (or the overlaid layer) to at or below the softening temperature of the material with the lowest softening temperature to form a reasonably strong and permanent bond between the re-solidified softened portions of the anisotropic elastic fibrous web 12 and the gatherable layers 24 and 28.

The bonder roller arrangement 34 may be a smooth anvil roller 36 and a patterned calender roller 38, such as, for example, a pin embossing roller arranged with the smooth anvil roller. One or both of the smooth anvil roller 36 and the calender roller 38 may be heated and the pressure between these two rollers may be adjusted by well-known means to provide the desired temperature, if any, and bonding pressure to join the gatherable layers to the elastic fibrous web. For some applications, both calender rollers may be smooth.

Figure 8:
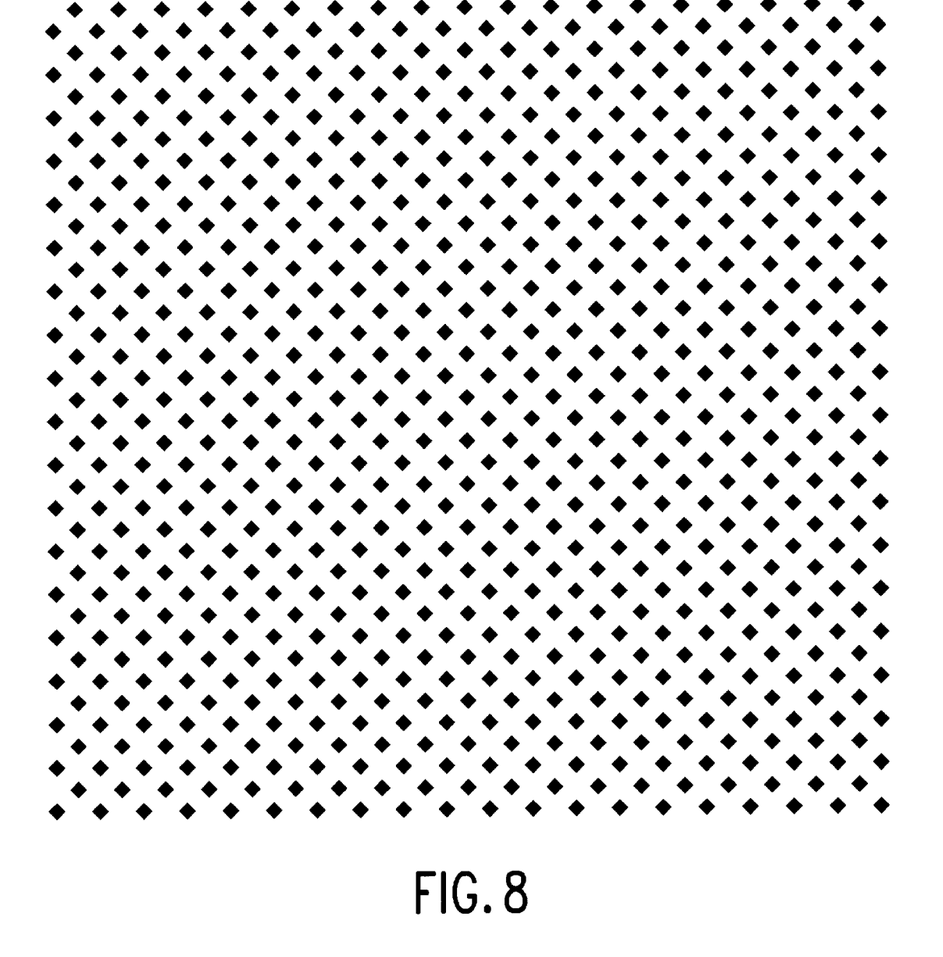
FIG. 8 shows a preferred calender bonding pattern used to bond together the anisotropic elastomeric web and extensible layers.

As can be appreciated, a preferred bonding between the extensible layers and the elastic sheet is point bonding. One suitable pattern for the pin embossing roller is known as the RAMISCH® pattern and is shown in FIG. 8. The RAMISCH® pattern is a deep, open pattern having a pin density of about 52 pins/in$^2$, a pin depth of about 0.052 in, and producing a bond area of about 8–14% of the total area between the bonded layers. Other bonding patterns can also be utilized. Various bonding patterns can be used, depending upon the desired tactile properties of the final composite laminate material. When the extensible layer is a nonwoven material such as, for example, spunbonded polypropylene, such bonding can be performed at temperatures as low as 60° F. A range of temperatures for the calender rolls during bonding between a gatherable layer such as, for example, spunbond polypropylene and an elastic sheet is 60° to 180° F.

For some applications, the bonding between the extensible layers and elastic fibrous web 12 need not be intermittent or patterned, but can be continuous. A variety of continuous bonding techniques known in the art can be employed, including without limitation various adhesive bonding techniques, smooth roll calender bonding, extrusion coating and extrusion lamination. Also, when the layers 24 and 28 are stretchable, the elastic web 12 need not be stretched prior to bonding the layers together.

With regard to bonding, one skilled in the art will appreciate that the temperature of the materials, or at least the bond sites thereof, depends on the temperature of the bonding roller(s) and whether or not they are heated, the existence or absence of other heat sources, the residence times, the compositions of the materials, the basis weights of the materials and their specific heats and thermal conductivities. One preferred bonding method for the present invention is autogenous bonding, during which the bonding rollers are applied to the layers under pressure but are not heated.

Conventional drive means and other conventional devices which may be utilized in conjunction with the apparatus of FIG. 1 are well known and, for purposes of clarity, have not been illustrated in the schematic view of FIG. 1.

Figures 3, 4, 5, 6, 7:
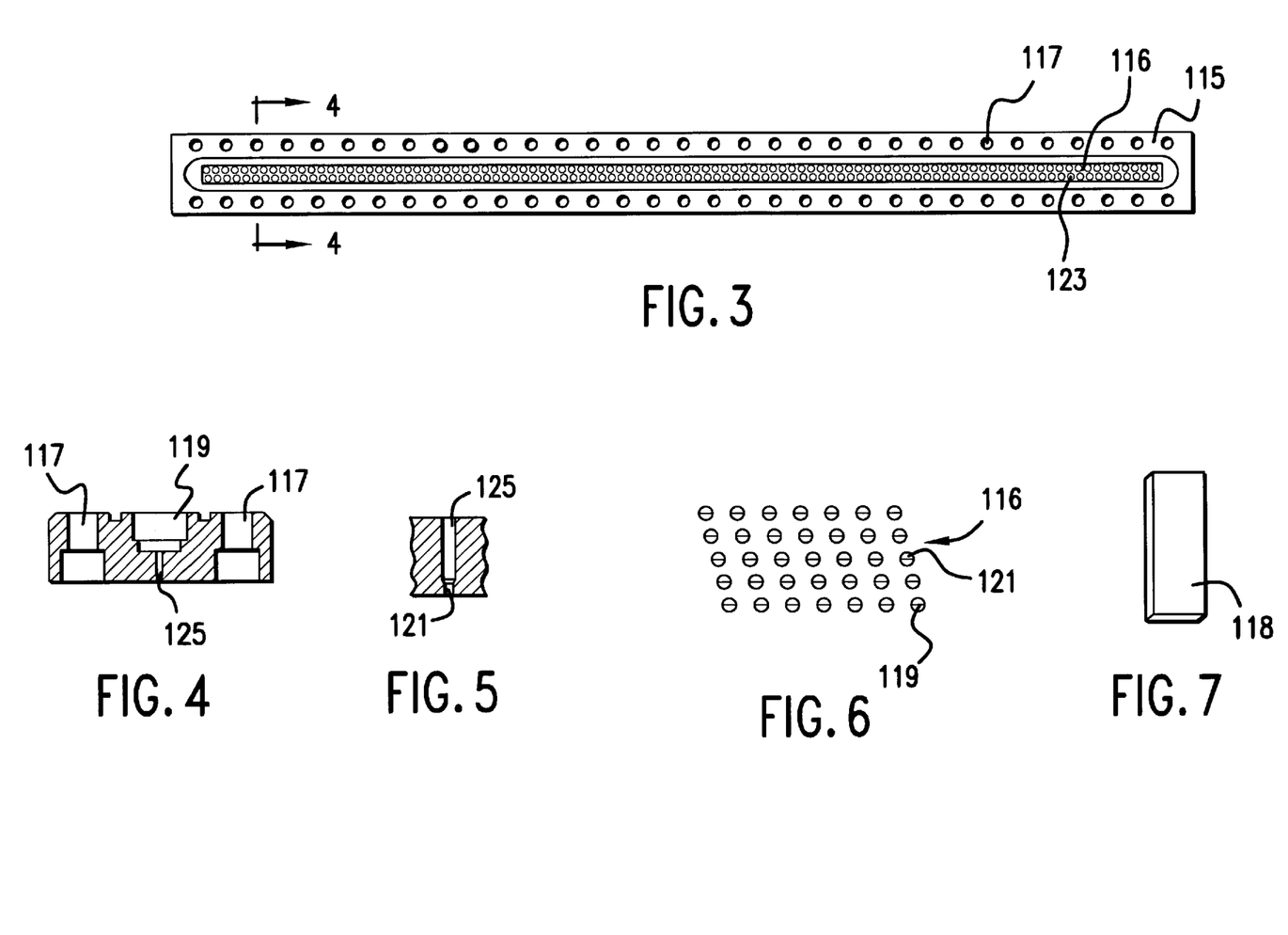
FIG. 3 is a plan view showing a spinnerette die head used to form the elastomeric ribbon-shaped elements.
FIG. 4 is a sectional view of the spinnerette die head taken along the line 4—4 in FIG. 3.
FIG. 5 is an expanded view of the capillary shown in FIG. 4.
FIG. 6 is an expanded view of the capillary section of the die head shown in FIG. 3.
FIG. 7 is a perspective view of an exemplary ribbon-shaped elastomeric element produced using the die head shown in FIG. 3.

An important component of the composite elastic material 40 is the anisotropic elastic fibrous web 12. The anisotropic elastic fibrous web 12 includes at least one layer of anisotropic elastomeric ribbon-shaped elements. Referring to FIG. 7, a single ribbon-shaped element 118 can be a filament having a width greater than its thickness. The "flatness ratio" of element 118 is the ratio of the maximum cross-sectional dimension of element 118 to the minimum cross-sectional dimension of element 118. The ribbon-shaped elements 118 forming the web 12 should, on average, have a flatness ratio of at least about 2.0, preferably at least about 4.0, more preferably at least about 6.0. In one preferred embodiment, the flatness ratio of the filaments 118 will, on average, be about 8.0.

The breathability, porosity or opacity of the anisotropic elastic fibrous web 12 (and of the composite elastic material 40) are influenced by the flatness ratios of the elements 118 as well as the element density (i.e., number of elements per cross-sectional square inch), element size and shape, and the amount of offset between elements in different layers (as explained further below). Elements 118 of higher flatness ratio will be closer to each other, resulting in less breathability to air and water vapor, and a more film-like web 12. Elements 118 with lower flatness ratios will tend to form a web 12 having higher breathability to both air and water vapor than a web of equal basis weight and element density having elements with higher flatness ratios. Other factors affecting breathability of the composite elastic material 40 include the presence or absence of a coating of elastic meltblown fibers onto the fibrous web 12, and the type of material 24 to which the elastic web 12 is laminated.

The sizes of the elements 118 may vary widely so long as their flatness ratios are such that the elements 118 are ribbon-shaped. When the elements 118 are spun filaments, the elements 118 may, on average, have a cross-sectional width of about 0.0025 to about 0.25 inch, preferably about 0.01 to about 0.15 inch, more preferably about 0.05 to about 0.10 inch. The thickness of the individual elements may, on average, range from about 0.0003 to about 0.05 inch, preferably about 0.001 to about 0.03 inch, more preferably about 0.005 to about 0.02 inch.

Figure 2:
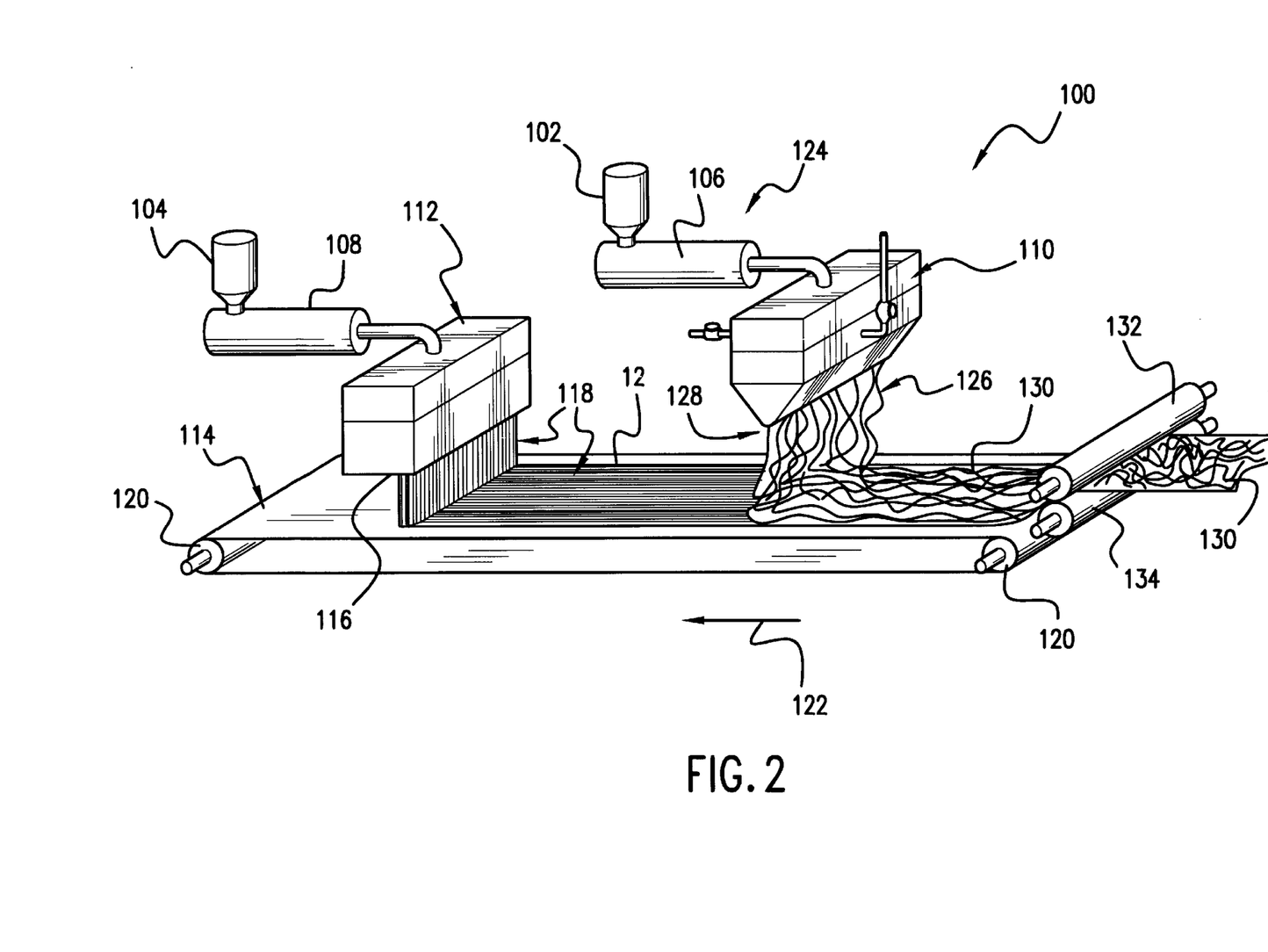
FIG. 2 is a schematic drawing of an exemplary process for forming an anisotropic elastomeric web having ribbon-shaped elements, and for coating the web having ribbon-shaped elements with a thin layer of elastic meltblown fibers.

FIG. 2 is a schematic view of a process for forming an anisotropic elastic fibrous web 12 which is used as a component of the composite elastic material of the present invention. The process is generally represented by reference numeral 100. In forming the web 12 of the elastic elements 118 (in this case, filaments) and, optionally, the coating of elastic meltblown fibers 126, pellets or chips, etc. (not shown) of an extrudable elastomeric polymer are introduced into a pellet hoppers 102 and 104 of extruders 106 and 108. When it is desired to form only the anisotropic elastic web 12 of elastic elements 118, the meltblowing extruder 106 and die 110 can be omitted from the process.

Each extruder has an extrusion screw (not shown) which is driven by a conventional drive motor (not shown). As the polymer advances through the extruder, due to rotation of the extrusion screw by the drive motor, it is progressively heated to a molten state. Heating the polymer to the molten state may be accomplished in a plurality of discrete steps with its temperature being gradually elevated as it advances through discrete heating zones of the extruder 106 toward a meltblowing die 110 and extruder 108 toward a continuous filament forming means 112. The meltblowing die 110 and the continuous filament forming means 112 may be yet another heating zone where the temperature of the thermoplastic resin is maintained at an elevated level for extrusion. Heating of the various zones of the extruders 106 and 108 and the meltblowing die 110 and the continuous filament forming means 112 may be achieved by any of a variety of conventional heating arrangements (not shown).

The elastomeric filament component of the anisotropic elastic fibrous web may be formed utilizing a variety of extrusion techniques. For example, the elastic filaments may be formed utilizing one or more conventional spinning or meltblowing die arrangements which has been modified to remove the gas streams (i.e., the primary air streams) which flow generally in the same direction as that of the extruded threads to attenuate the extruded threads and which has been further modified, as explained below, to have slotlike openings for the production of ribbon-shaped filaments. The illustrated modified spinning die arrangement 112 extends across a foraminous collecting surface 114 in a direction which is substantially transverse to the direction of movement of the collecting surface 114. The modified die arrangement 112 includes a linear array 116 of slotted capillaries aligned along the transverse extent of the die with the transverse extent of the die being approximately as long as the desired width of the parallel rows of elastomeric filaments which is to be produced. That is, the transverse dimension of the die is the dimension which is defined by the linear array of slotted die capillaries.

FIG. 3 illustrates the die face 115 having the array 116 of slotted capillaries disposed in an elongated extrusion portion 123. The die face 115 is held in place using a plurality of fastener elements 117, which can be bolts or the like, disposed along its outer perimeter.

FIG. 6 shows how the array 116 of individual capillaries 119 is arranged in parallel rows. In the embodiment shown, there are five such parallel rows of capillaries 119. The extrusion portion 123 of the die face 115 is about 60 inches long and about 1 inch wide. There are about eighteen of the capillaries 119 for each one inch cross-directional length of the extrusion portion 123, or about 3.6 capillaries per row for each one inch of cross-directional length.

Each capillary 119 has a slotted opening 121 for producing a ribbon-shaped filament 118 as shown in FIG. 7. Also, the rows of capillaries 119 may be offset as shown, so that the slots in each row overlap the edges of the slots in the adjacent row or rows. The amount of offset can be varied to control breathability and other properties of the web 12. The slotted openings 121 should have shapes and aspect ratios which correspond substantially to the shapes and flatness ratios of the filaments 118.

Typically, the slotted openings 121 will have aspect ratios of at least about 2.0, preferably at least about 4.0, more preferably at least about 6.0. The length of each slotted opening 121 (corresponding to the initial width of the ribbon-shaped filament before drawdown) may range from about 0.005–0.5 inch, preferably about 0.02–0.3 inch, more preferably about 0.1–0.2 inch. The width of each slotted opening 121 (corresponding to the thickness of the filament 118) may be about 0.0006–0.1 inch, preferably about 0.002–0.06 inch, more preferably about 0.01–0.04 inch. Depending on the size of the die, from about 2–240 capillaries 119 can be provided per linear inch of die face. The extrusion portion 123 of the die can range from about 5 to about 150 or more inches in length. A drawdown ratio for the filaments may range from about 1.1:1 to about 10:1, desirably about 1.5:1 to about 5:1.

FIG. 4 shows a capillary 119 in cross-section, and FIG. 5 shows only the lower portion 125 including the slotted opening 121 of the capillary. The capillary 119 may be more or less cylindrical at all locations above the slotted opening 121. As shown in FIGS. 4 and 5, the capillary 119 may have a funnel-like cross-section, shown by a progressively narrower cross-section approaching the lower portion 125 and slotted opening 121.

Since the heated gas stream (i.e., the primary air stream) which flows past the die tip is greatly reduced or absent, it is desirable to insulate the die tip or provide heating elements to ensure that the extruded polymer remains molten and flowable while in the die tip. Polymer is extruded from the array 116 of capillaries in the modified die 112 to create extruded ribbon-shaped elastomeric filaments 118.

The extruded elastomeric ribbon-shaped filaments 118 have an initial velocity as they leave the array 116 of capillaries in the modified die 112. These filaments 118 are deposited upon a foraminous surface 114 which should be moving at least at the same velocity as the initial velocity of the elastic filaments 118. This foraminous surface 114 is an endless belt conventionally driven by rollers 120. The filaments 118 are deposited in machine direction alignment on the surface of the endless belt 114 which is rotating as indicated by the arrow 122 in FIG. 2. Vacuum boxes (not shown) may be used to assist in retention of the matrix on the surface of the belt 114. The tip of the die 112 should be as close as practical to the surface of the foraminous belt 114 upon which the continuous elastic filaments 118 are collected. For example, this forming distance may be from about 1 inch to about 10 inches. Desirably, this distance is from about 1 inch to about 8 inches.

It may be desirable to have the foraminous surface 114 moving at a speed that is much greater than the initial velocity of the elastic filaments 118 in order to enhance the alignment of the filaments 118 in the machine direction and/or elongate the filaments 118 so they achieve a desired diameter. For example, alignment of the elastomeric filaments 118 may be enhanced by having the foraminous surface 114 move at a velocity from about 2 to about 7 times greater than the initial velocity of the elastomeric filaments 118. Even greater speed differentials may be used if desired. While different factors will affect the particular choice of velocity for the foraminous surface 114, it will typically be from about 3 to about 6 times faster than the initial velocity of the elastomeric filaments 118.

Desirably, the continuous elastomeric filaments are formed at a density per inch of width of material which corresponds generally to the density of capillaries on the die face. For example, the filament density per inch of width of material may range from about 2 to about 240 such filaments per inch width of material. Typically, lower densities of filaments (e.g., 2–35 filaments per inch of width) may be achieved with only one filament forming die. Higher densities (e.g., 35–240 filaments per inch of width) may be achieved with multiple banks of filament forming equipment.

Figure 9:
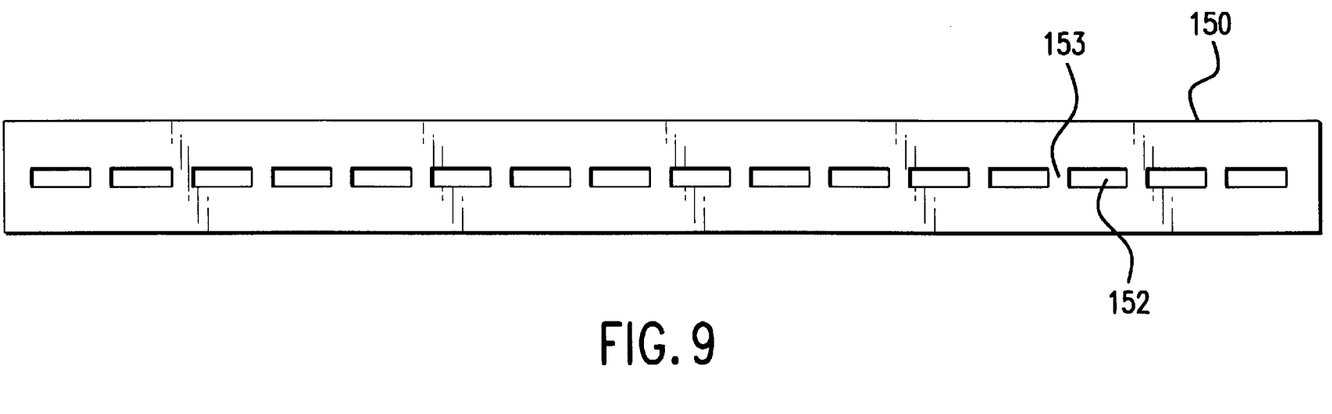
FIG. 9 is a plan view showing a cast extrusion die which can alternatively be used to form elastomeric ribbon-shaped elements having relatively large sizes.

In an alternative embodiment, the elastomeric ribbon-shaped elements may be formed using a conventional cast extrusion die which has been intermittently plugged or otherwise modified to permit the extrusion of a plurality of film strips. FIG. 9 illustrates a cast extrusion die 150 having numerous individual slots 152 for the extrusion of film strips. The die 150 may be formed, for instance, by modifying a conventional cast film extrusion die to further include a plurality of plugs in the regions 153 that separate the individual slots 152. The modified cast extrusion die may be used to produce somewhat larger ribbon-shaped elements than are produced using the modified spinning process described above. For instance, the individual film strips may have an extruded width (after drawdown) of about 0.10–1.0 inch, suitably about 0.20–0.80 inch, desirably about 0.30–0.70 inch. The film strips may have a thickness of about 0.02–0.20 inch, suitably about 0.04–0.16 inch, desirably about 0.08–0.12 inch.

The elastomeric ribbon-shaped elements produced from the cast extrusion die 150 may be laid down onto a collecting surface similar to the foraminous conveyor system 114 shown in FIG. 2. Again, drawdown may be effected by varying the speed of the collecting surface 114 relative to the speed of extrusion of the ribbon-shaped elements. A drawdown ratio for the elastomeric film strips may range from about 1.1:1 to about 10:1, desirably about 1.5:1 to about 5:1. The elastomeric film strips are extruded generally parallel to one another in the machine direction of the collecting surface, and are generally spaced apart from each other. The distance between the ribbon-shaped film strips on the collecting surface (after drawdown) may suitably range from about 0.1–2.0 inches, desirably about 0.5–1.0 inch.

When the elastomeric ribbon-shaped elements are cast from a film die, they will generally be deposited in a single layer onto the collecting surface. The die slots 152 may be somewhat larger than the ultimate film strip dimensions, to accommodate the drawdown. For example, each die slot 152 may have a cross-direction length of about 0.25–2.5 inch, suitably about 0.50–2.0 inch, desirably about 0.75–1.75 inch. The thickness of the die slots 152 may be about 0.05–0.50 inch, suitably about 0.10–0.40 inch, desirably about 0.12–0.30 inches.

One objective of producing larger ribbon-shaped elements is to ensure that the filaments have a width that is larger than the individual bonds produced by a point bonding apparatus used to bond the elastomeric web to one or more extensible layers. The point bonding may partially destroy the elastic elements. If the ribbon-shaped elements are wider than the point bonds, then no ribbon-shaped elastic element is totally destroyed across its width.

The elastomeric anisotropic fibrous web 12 having ribbon-shaped elements may optionally be coated with a layer of conventional elastomeric meltblown fibers 126 to form an anisotropic elastomeric composite 130 (FIG. 2) which is then intermittently bonded to the gatherable layer 24 (FIG. 1). Alternatively, the elastomeric web 12 having ribbon-shaped elements can be laminated directly to the extensible layers 24 and 28 without the intermediate coating step. When the elastomeric web 12 is coated with elastomeric meltblown fibers 126, the resulting anisotropic elastomeric composite 130 may contain at least about 20% by weight of the ribbon-shaped elements contributed by the elastomeric anisotropic fibrous web 12. For example, the elastomeric anisotropic composite 130 may contain about 20–95% by weight of the layer 12 of ribbon-shaped elastomeric elements and about 5–80% by weight of the layer 126 of conventional elastomeric meltblown fibers. Desirably, the anisotropic elastomeric composite 130 may contain about 50–95% by weight of the layer 12 of ribbon-shaped elastomeric elements and about 5–50% by weight of the layer 126 of conventional elastomeric meltblown fibers. More desirably, the anisotropic elastomeric composite 30 may contain about 80–95% by weight of the layer 12 of ribbon-shaped elastomeric filaments and about 5–20% by weight of the layer 126 of conventional elastomeric meltblown fibers.

When added, the meltblown fiber component of the anisotropic elastic fibrous composite web is formed utilizing a conventional meltblowing process represented by reference numeral 124. Meltblowing processes generally involve extruding a thermoplastic polymer resin through a plurality of small diameter capillaries of a meltblowing die as molten threads into a heated gas stream (the primary air stream) which is flowing generally in the same direction as that of the extruded threads so that the extruded threads are attenuated (i.e., drawn or extended) to reduce their diameter. Such meltblowing techniques, and apparatus therefor, are discussed fully in U.S. Pat. No. 4,663,220, the contents of which are incorporated herein by reference.

In the meltblown die arrangement 110, the position of air plates which, in conjunction with a die portion define chambers and gaps, may be adjusted relative to the die portion to increase or decrease the width of the attenuating gas passageways so that the volume of attenuating gas passing through the air passageways during a given time period can be varied without varying the velocity of the attenuating gas. Generally speaking, lower attenuating gas velocities and wider air passageway gaps are preferred if substantially continuous meltblown fibers or microfibers are to be produced.

The two streams of attenuating gas converge to form a stream of gas which entrains and attenuates the molten threads, as they exit the orifices, into fibers or, depending upon the degree of attenuation, microfibers, of a small diameter which is usually less than the diameter of the orifices. The gas-borne fibers or microfibers 126 are blown, by the action of the attenuating gas, onto a collecting arrangement which, in the embodiment illustrated in FIG. 2, is the foraminous endless belt 114 which carries the elastomeric filaments in machine direction alignment. The fibers or microfibers 126 are collected as a coherent matrix of fibers on the surface of the elastomeric filaments 118 and foraminous endless belt 114 which is rotating as indicated by the arrow 122 in FIG. 2. If desired, the meltblown fibers or microfibers 126 may be collected on the foraminous endless belt 114 at numerous impingement angles. Vacuum boxes (not shown) may be used to assist in retention of the matrix on the surface of the belt 114. Typically the tip 128 of the die 110 is from about 6 inches to about 14 inches from the surface of the foraminous belt 116 upon which the fibers are collected. The entangled fibers or microfibers 126 autogenously bond to at least a portion of the elastic continuous filaments 18 because the fibers or microfibers 126 are still somewhat tacky or molten while they are deposited on the elastic continuous filaments 118, thereby forming the anisotropic elastic fibrous web 130.

At this point, it may be desirable to lightly calender the composite elastic fibrous web of meltblown fibers and ribbon-shaped filaments in order to enhance the autogenous bonding. This calendering may be accomplished with a pair of patterned or un-patterned pinch rollers 132 and 134 under sufficient pressure (and temperature, if desired) to cause permanent autogenous bonding between the ribbon-shaped elastomeric filaments and the elastomeric meltblown fibers.

As discussed above, the ribbon-shaped filaments and elastomeric meltblown fibers are deposited upon a moving foraminous surface. In one embodiment of the invention, meltblown fibers are formed directly on top of the extruded ribbon-shaped elastomeric filaments. This is achieved by passing the filaments and the foraminous surface under equipment which produces meltblown fibers. Alternatively, a layer of elastomeric meltblown fibers may be deposited on a foraminous surface and substantially parallel rows of ribbon-shaped elastomeric filaments may be formed directly upon the elastomeric meltblown fibers. Various combinations of filament forming and fiber forming equipment may be set up to produce different types of elastic fibrous webs. For example, the elastic fibrous web may contain alternating layers of elastomeric ribbon-shaped filaments and elastomeric meltblown fibers. Several dies for forming meltblown fibers or creating ribbon-shaped elastomeric filaments may also be arranged in series to provide superposed layers of fibers or filaments.

The elastomeric meltblown fibers and elastomeric ribbon-shaped filaments may be made from any material which may be manufactured into such fibers and filaments. Generally, any suitable elastomeric fiber forming resins or blends containing the same may be utilized for the elastomeric meltblown fibers and any suitable elastomeric filament forming resins or blends containing the same may be utilized for the elastomeric filaments. The fibers and filaments may be formed from the same or different elastomeric resin. The fibers and/or filaments may also be bicomponent and/or biconstituent, as defined above.

For example, the elastomeric meltblown fibers and/or the elastomeric filaments may be made from block copolymers having the general formula A-B-A' where A and A' are each a thermoplastic polymer endblock which contains a styrenic moiety such as a poly (vinyl arene) and where B is an elastomeric polymer midblock such as a conjugated diene or a lower alkene polymer. The block copolymers may be, for example, (polystyrene/poly(ethylene-butylene)/polystyrene) block copolymers available from the Shell Chemical Company under the trademark KRATON®G. One such block copolymer may be, for example, KRATON®G-1657.

Other exemplary elastomeric materials which may be used include polyurethane elastomeric materials such as, for example, those available under the trademark ESTANE from B. F. Goodrich & Co., polyamide elastomeric materials such as, for example, those available under the trademark PEBAX® from the Rilsan Company, and polyester elastomeric materials such as, for example, those available under the trade designation Hytrel from E.I. DuPont De Nemours & Company. Formation of elastomeric meltblown fibers from polyester elastic materials is disclosed in, for example, U.S. Pat. No. 4,741,949 to Morman et al., hereby incorporated by reference. Useful elastomeric polymers also include, for example, elastic copolymers of ethylene and at least one vinyl monomer such as, for example, vinyl acetates, unsaturated aliphatic monocarboxylic acids, and esters of such monocarboxylic acids. The elastic copolymers and formation of elastomeric meltblown fibers from those elastic copolymers are disclosed in, for example, U.S. Pat. No. 4,803,117.

Other useful elastomers include constrained geometry-catalyzed and/or metallocene-catalyzed elastomeric materials, including constrained geometry polyolefins produced and sold by the Dow Chemical Company under the trade name ELITE®. One useful constrained geometry-catalyzed elastomer is a linear low density polyethylene sold under the trade name ELITE® 5800.02. Metallocene-catalyzed polymers and constrained geometry catalyzed polymers are further described in Kirk-Othmer's "*Encyclopedia of Chemical Technology*," Fourth Edition (1996), Vol. 17, pp. 765–767, the disclosure of which is incorporated by reference.

Processing aids may be added to the elastomeric polymer. For example, a polyolefin may be blended with the elastomeric polymer (e.g., the A-B-A elastomeric block copolymer) to improve the processability of the composition. The polyolefin must be one which, when so blended and subjected to an appropriate combination elevated pressure and elevated temperature conditions, extrudable, in blended form, with the elastomeric polymer. Useful blending polyolefin materials include, for example, polyethylene, polypropylene and polybutene, including ethylene copolymers, propylene copolymers and butene copolymers. A particularly useful polyethylene may be obtained from the U.S.I. Chemical Company under the trade designation PETROTHENE®NA 601 (also referred to herein as PE NA 601 or polyethylene NA 601). Two or more of the polyolefins may be utilized. Extrudable blends of elastomeric polymers and polyolefins are disclosed in, for example, previously referenced U.S. Pat. No. 4,663,220.

Desirably, the elastomeric meltblown fibers and/or the ribbon-shaped elastomeric elements should have some tackiness to enhance autogenous bonding. For example, the elastomeric polymer itself may be tacky when formed into fibers and/or filaments or, alternatively, a compatible tackifying resin may be added to the extrudable elastomeric compositions described above to provide tackified elastomeric fibers and/or filaments that autogenously bond. In regard to the tackifying resins and tackified extrudable elastomeric compositions, note the resins and compositions as disclosed in U.S. Pat. No. 4,787,699, hereby incorporated by reference.

Any tackifier resin can be used which is compatible with the elastomeric polymer and can withstand the high processing (e.g., extrusion) temperatures. If the elastomeric polymer (e.g., A-B-A elastomeric block copolymer) is blended with processing aids such as, for example, polyolefins or extending oils, the tackifier resin should also be compatible with those processing aids. Generally, hydrogenated hydrocarbon resins are preferred tackifying resins, because of their better temperature stability. REGALREZ™ and ARKON™ series tackifiers are examples of hydrogenated hydrocarbon resins. ZONATAK™ 501 lite is an example of a terpene hydrocarbon. REGALREZ™ hydrocarbon resins are available from Himont Incorporated. ARKON™ series resins are available from Arakawa Chemical (U.S.A.) Incorporated. Of course, the present invention is not limited to use of such three tackifying resins, and other tackifying resins which are compatible with the other components of the composition and can withstand the high processing temperatures, can also be used.

Typically, the blend used to form the elastomeric elements and meltblown fibers include, for example, from about 40 to about 80 percent by weight elastomeric polymer, from about 5 to about 40 percent polyolefin and from about 5 to about 40 percent resin tackifier. For example, a particularly useful composition designated KRATON® G-2755 includes, by weight, about 61 to about 65 percent KRATON® G-1657, about 17 to about 23 percent polyethylene PETROTHENE® NA 601, and about 15 to about 20 percent REGALREZ™ 1126 tackifier. REGALREZ™ 1126 is a hydrogenated styrene-based tackifying resin. KRATON® G-2760 is another useful blend of a block copolymer (KRATON®G-1730M) and tackifier.

The elastomeric meltblown fiber component of the present invention may be a mixture of elastic and nonelastic fibers or particulates. For an example of such a mixture, reference is made to U.S. Pat. No. 4,209,563, incorporated herein by reference, in which elastomeric and non-elastomeric fibers are commingled to form a single coherent web of randomly dispersed fibers. Another example of such an elastic composite web would be one made by a technique such as disclosed in previously referenced U.S. Pat. No. 4,741,949. That patent discloses an elastic nonwoven material which includes a mixture of meltblown thermoplastic fibers and other materials. The fibers and other materials are combined in the gas stream in which the meltblown fibers are borne so that an intimate entangled commingling of meltblown fibers and other materials, e.g., wood pulp, staple fibers or particulates such as, for example, activated charcoal, clays, starches, or hydrocolloid (hydrogel) particulates commonly referred to as super-absorbents occurs prior to collection of the fibers upon a collecting device to form a coherent web of randomly dispersed fibers.

When the elastomeric ribbon-shaped elements are formed from a cast extrusion die instead of a spinning die, the ribbon-shaped film strips are typically not coated with meltblown fibers. Whether or not the ribbon-shaped elements are coated with meltblown fibers, the adhesion between the elastomeric web 12 and the extensible layers 24 and 28 may be enhanced by coating the contact surface of each extensible layer with an adhesive resin. A suitable adhesive resin is sold under the trade name Findlay Adhesive 2525A, and is a KRATON®-based (i.e. styrene butadiene rubber-based) adhesive. Suitably, the adhesive may be spray coated onto the surface of the extensible layers to be contacted with the elastomeric web 12. The coating may have a basis weight of about 1–10 grams per square meter, desirably about 3–5 grams per square meter. Other adhesives, and other application techniques, may also be employed.

Figure 10:
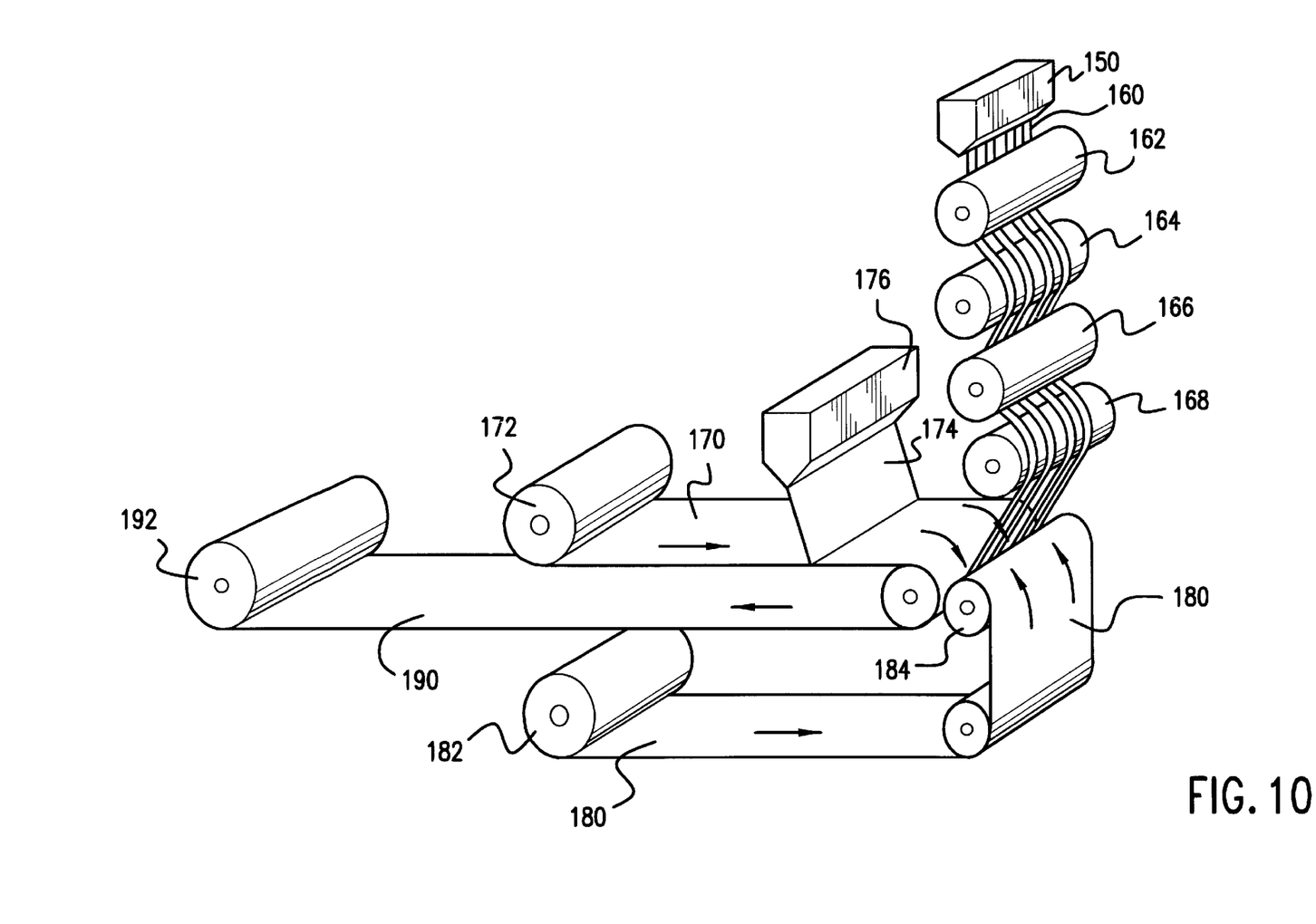
FIG. 10 is a schematic drawing of another exemplary process for forming a composite elastic material of the invention.

FIG. 10 shows another exemplary process for making a composite elastic material of the invention, useful when the ribbon-shaped filaments are produced with a cast film extrusion die. Ribbon-shaped elastomeric filaments 160 (i.e. cast film strips) are extruded from the modified cast film extrusion die 150, and are quenched using chill rollers 162, 164, 166 and 168. A first extensible layer 170 which can, for instance, be an extensible nonwoven web, is unwound from a storage roll 172 and is coated on one surface with an adhesive 174 using an adhesive dispenser 176 which can, for instance, be a meltblowing or melt spraying apparatus. A second extensible layer 180 which can, for instance, be an extensible nonwoven web, is unwound from a second supply roll 182 and is also coated with adhesive from a dispensing apparatus (not shown).

The adhesive-coated extensible layers 170 and 180 are joined with the layer of ribbon-shaped elastic filaments 160 sandwiched between them, with the adhesive-coated surfaces of the extensible layers 170 and 180 contacting the ribbon-shaped elastic filaments 160. The layers are bonded together between a pair of calender rollers 184. The calender rollers 184 may be heated or unheated, depending on the type of adhesive used. The calender rollers 184 may be patterned or smooth, and may impart spaced-apart bond regions or continuous bonding to the layers, depending on whether the extensible layers 170 and 180 are non-stretchable gatherable layers (requiring spaced-apart bonding to effect gathering) or stretchable layers (in which case, the bonding may be continuous or spaced apart). Also, the calender rollers 184 may or may not rotate at a speed sufficient to stretch the elastic filaments 160, depending on whether the extensible layers 170 and 180 are gatherable (requiring stretching of filaments 160 prior to bonding) or stretchable (not requiring prestretching of filaments 160).

The resulting composite elastic material 190 is thereby produced, and can be wound onto a storage roller 192.

While the embodiments of the invention disclosed herein are generally considered preferred, various improvements and modifications can be made without departing from the spirit and scope of the invention. The scope of the invention is indicated by the appended claims, and all changes that fall within the meaning and range of equivalents are intended to be embraced therein.

We claim:

1. A composite elastic material, comprising:
   an anisotropic elastomeric polymer structure including a layer of at least 10 ribbon-shaped elastomeric elements; and
   an extensible layer joined using point bonds to the anisotropic elastomeric polymer structure so that the extensible layer gathers or retracts when the elastomeric structure is relaxed;
   wherein the ribbon-shaped elastomeric elements are wider than the point bonds.

2. The composite elastic material of claim 1, wherein the ribbon-shaped elastomeric elements have a flatness ratio of at least about 2.0.

3. The composite elastic material of claim 1, wherein the ribbon-shaped elastomeric elements have a flatness ratio of at least about 4.0.

4. The composite elastic material of claim 1, wherein the ribbon-shaped elastomeric elements have a flatness ratio of at least about 6.0.

5. The composite elastic material of claim 1, wherein the ribbon-shaped elastomeric elements comprise filaments.

6. The composite elastic material of claim 5, wherein the ribbon-shaped elements have a cross-sectional width of about 0.0025–0.25 inch.

7. The composite elastic material of claim 5, wherein the ribbon-shaped elements have a cross-sectional width of about 0.01–0.15 inch.

8. The composite elastic material of claim 5, wherein the ribbon-shaped elements have a cross-sectional width of about 0.05–0.10 inch.

9. The composite elastic material of claim 1, wherein the ribbon-shaped elements comprise extruded film strips.

10. The composite elastic material of claim 9, wherein the ribbon-shaped elements have a cross-sectional width of about 0.10–1.0 inch.

11. The composite elastic material of claim 9, wherein the ribbon-shaped elements have a cross-sectional width of about 0.20–0.80 inch.

12. The composite elastic material of claim 9, wherein the ribbon-shaped elements have a cross-sectional width of about 0.30–0.70 inch.

13. The composite elastic material of claim 1, wherein the ribbon-shaped elastomeric filaments comprise an elastomer selected from the group consisting of elastic polyesters, elastic polyurethanes, elastic polyamides, elastic copolymers of ethylene and at least one vinyl monomer, elastic metallocene-catalyzed polyolefins, and elastic A-B-A' block copolymers wherein A and A' are the same or different thermoplastic polymers, and wherein B is an elastomeric polymer block.

14. The composite elastic material of claim 1, wherein the extensible layer comprises a gatherable layer joined at spaced-apart locations to the anisotropic elastomeric polymer structure so that the gatherable layer is gathered between the spaced-apart locations when the elastomeric structure is relaxed.

15. The composite elastic material of claim 14, wherein the gatherable layer comprises a nonwoven web of fibers.

16. The composite elastic material of claim 15, wherein the gatherable nonwoven web is selected from the group consisting of a spunbond web, a meltblown web, a carded web, and a multilayer web including at least one of the foregoing nonwoven webs.

17. The composite elastic material of claim 14, wherein the gatherable layer comprises a thermoplastic film.

18. The composite elastic material of claim 1, wherein the extensible layer comprises a stretchable layer joined to the anisotropic elastomeric polymer structure so that the stretchable layer is retracted when the elastomeric structure is relaxed.

19. The composite elastic material of claim 18, wherein the stretchable layer is selected from the group consisting of knitted structures, woven structures, creped papers, extensible nonwoven fabrics, compressively preshrunk fabrics, and extensible thermoplastic films.

20. The composite elastic material of claim 1, wherein the ribbon-shaped elements are arranged in a plurality of layers.

21. The composite elastic material of claim 1, wherein the ribbon-shaped elements are aligned in the machine direction.

22. The composite elastic material of claim 1, comprising two of the extensible layers joined on both sides of the anisotropic elastomeric polymer structure.

23. A composite elastic material, comprising:
   an anisotropic elastomeric polymer structure including at least one layer of elastomeric ribbon-shaped elements and at least one layer of elastomeric meltblown fibers bonded to at least a portion of the elastomeric ribbon-shaped elements; and
   at least one extensible layer joined using point bonds at spaced-apart locations to the ribbon-shaped elements of the anisotropic elastomeric polymer structure so that the extensible layer gathers or retracts when the anisotropic elastomeric polymer structure is relaxed;
   wherein the ribbon-shaped elements are wider than the point bonds.

24. The composite elastic material of claim 23, wherein the elastomeric ribbon-shaped elements are arranged in machine direction alignment.

25. The composite elastic material of claim 24, wherein the elastomeric meltblown fibers are aligned in the machine direction.

26. The composite elastic material of claim 23, wherein the layer of elastomeric meltblown fibers comprises a mixture of elastomeric meltblown fibers and one or more materials selected from the group consisting of wood pulp, inelastic fibers, particulates, superabsorbent materials, and combinations thereof.

27. The composite elastic material of claim 23, wherein the ribbon-shaped elements have a flatness ratio of at least about 2.0.

28. The composite elastic material of claim 23, wherein the ribbon-shaped elements have a flatness ratio of at least about 4.0.

29. The composite elastic material of claim 23, wherein the ribbon-shaped elements have a flatness ratio of at least about 6.0.

30. The composite elastic material of claim 23, wherein the elastomeric ribbon-shaped elements comprise polymer filaments.

31. The composite elastic material of claim 23, wherein the extensible layer comprises a gatherable layer joined at spaced apart locations to the anisotropic elastomeric polymer structure so that the gatherable layer is gathered between the spaced-apart locations when the elastomeric structure is relaxed.

32. The composite elastic material of claim 23, wherein the extensible layer comprises a stretchable layer joined to the anisotropic elastomeric polymer structure so that the stretchable layer is retracted when the elastomeric structure is relaxed.

33. The composite elastic material of claim 23, comprising two of the extensible layers joined to the anisotropic elastomeric polymer structure.

34. The composite elastic material of claim 23, wherein the ribbon-shaped elastomeric elements and the elastomeric meltblown fibers each comprise the same or different polymers selected from the group consisting of elastic polyesters, elastic polyurethanes, elastic polyamides, elastic copolymers of ethylene and at least one vinyl monomer, elastic metallocene-catalyzed polyolefins, and elastic A-B-A' block copolymers wherein A and A' are the same or different thermoplastic polymers, and wherein B is an elastomeric polymer block.

35. The composite elastic material of claim 31, wherein the gatherable layer comprises a nonwoven web of fibers.

36. The composite elastic material of claim 35, wherein the gatherable nonwoven web is selected from the group consisting of a spunbond web, a meltblown web, a carded web, and a multilayer web including at least one of the foregoing nonwoven webs.

37. The composite elastic material of claim 32, wherein the stretchable layer comprises a material selected from the group consisting of knitted structures, woven structures, creped papers, extensible nonwoven fabrics, and compressively preshrunk fabrics.

38. A method of making a composite elastic material, comprising the steps of:
   forming a layer of ribbon-shaped elastomeric elements in machine direction alignment on a conveyor;
   stretching the layer of ribbon-shaped elastomeric elements;
   joining the stretched layer of ribbon-shaped elastomeric elements to a gatherable layer, and bonding the layers together at spaced-apart locations using point bonds, wherein the ribbon-shaped elastomeric elements are wider than the point bonds; and
   relaxing the layer of ribbon-shaped elastomeric elements so that the gatherable layer gathers between the bonding locations.

39. The method of claim 38, further comprising the steps of bonding a layer of meltblown elastomeric filaments to the layer of ribbon-shaped elastomeric elements to form an anisotropic elastomeric composite, and joining and bonding the anisotropic elastomeric composite to the gatherable layer.

40. A method of making a composite elastic material, comprising the steps of:
   forming a layer of ribbon-shaped elastomeric elements in machine direction alignment on a conveyor; and
   joining the layer of ribbon-shaped elastomeric elements to a stretchable layer using point bonds;
   wherein the ribbon-shaped elastomeric elements are wider than the point bonds, and the stretchable layer is in a stretched state when the ribbon-shaped elastomeric elements are stretched, and is in a retracted state when the ribbon-shaped elastomeric elements are relaxed.

* * * * *